(12) United States Patent  (10) Patent No.: US 7,887,184 B2
Baer et al.  (45) Date of Patent: Feb. 15, 2011

(54) METHOD AND APPARATUS FOR OBTAINING THE DISTANCE FROM AN OPTICAL MEASUREMENT INSTRUMENT TO AN OBJECT UNDER TEST

(75) Inventors: C. David Baer, Albuquerque, NM (US); Daniel R. Neal, Tijeras, NM (US); Richard James Copland, Albuquerque, NM (US); David Austin Neal, Albuquerque, NM (US)

(73) Assignee: AMO Wavefront Sciences LLC., Santa Ana, CA (US)

( * ) Notice: Subject to any disclaimer, the term of this patent is extended or adjusted under 35 U.S.C. 154(b) by 543 days.

(21) Appl. No.: 11/938,145

(22) Filed: Nov. 9, 2007

(65) Prior Publication Data

US 2008/0291396 A1 Nov. 27, 2008

Related U.S. Application Data

(60) Provisional application No. 60/857,776, filed on Nov. 9, 2006.

(51) Int. Cl.
*A61B 3/14* (2006.01)
*A61B 3/10* (2006.01)
*A61B 3/00* (2006.01)

(52) U.S. Cl. .................. 351/208; 351/211; 351/221; 351/246

(58) Field of Classification Search .................. 351/211, 351/200, 205, 208, 221, 246; 356/4.01, 4.03, 356/4.04
See application file for complete search history.

(56) References Cited

U.S. PATENT DOCUMENTS 5,165,063 A 11/1992 Strater et al.
6,002,484 A 12/1999 Rozema et al.

FOREIGN PATENT DOCUMENTS

EP 0 142 464 A1 9/1984
EP 1 223 406 A1 7/2002

OTHER PUBLICATIONS

F. Pedroti et al., "Optik fur ingenieure-grudlagen," 2005, Springer, XP00478814, pp. 115-143.

*Primary Examiner*—Jack Dinh (57) ABSTRACT

Systems and methods for measuring a distance from a reference plane of an optical measurement instrument to a reference plane of an optical device under test are disclose. In one embodiment a system for measuring this distance includes an illumination system, an optical system, and optical sensor and a processor. The illumination system is configured or adapted to illuminate the object under test. The optical system is configured or adapted to receive light from the object under test and to produce an aberrated image. The optical sensor is configured or adapted to receive and sense the aberrated image. The processor determines the distance from the reference plane of the optical measurement instrument to the reference plane of the optical device based on an aspect of the aberrated image sensed by the optical sensor.

23 Claims, 9 Drawing Sheets

METHOD AND APPARATUS FOR OBTAINING THE DISTANCE FROM AN OPTICAL MEASUREMENT INSTRUMENT TO AN OBJECT UNDER TEST

CROSS-REFERENCES TO RELATED APPLICATIONS

This patent application claims priority under 35 U.S.C. §119 of U.S. provisional patent application 60/857,776 filed on 9 Nov. 2006, the entirety of which is hereby incorporated by reference for all purposes as if fully set forth herein.

BACKGROUND AND SUMMARY

1. Field

This invention relates generally to the field of optical measurement instruments, such as eye examination instruments, and more particularly an apparatus and method for measuring or computing the distance from an object under test (e.g., an eye) to an optical or mechanical reference plane of a measurement instrument.

2. Description

Optical measurement instruments, such as instruments which measure the optical properties of the human eye, rely on the correct working distance being set between a reference plane of the instrument and a reference plane of the object being measured, so that the best possible imaging conditions are met, resulting in the highest possible accuracy of the instrument. A misalignment of this distance (hereinafter referred to as the "Z-Distance") can result in measurement inaccuracies. In the case of corneal topography, keratometry and wavefront aberration measurements the result can be a misinterpretation of the radius of curvature of either a surface or waves of light, or error in measurement of other parameters such as ocular refraction, higher order aberrations or pupil size. These inaccuracies will furthermore be of unknown magnitude, due to the unknown error in the Z-distance.

Accordingly, it would be advantageous to provide an arrangement that can be used to determine accurately the distance between a reference plane of an optical measurement instrument and a reference plane of an object under test. It would further be advantageous to provide such an arrangement that can be in a standalone configuration, or integrated into the optical measurement instrument.

It would also be advantageous to provide a method for accurately measuring or computing the distance from a surface of an eye or other object under test to an optical or mechanical reference plane of a measurement instrument. Other and further objects and advantages will appear hereinafter.

In one aspect of the invention, a method is provided for measuring the distance from a reference plane of an optical measurement instrument to a reference plane of an object under test. The method comprises: illuminating the object under test with a source; passing light from the object under test through an optical system to produce an aberrated image of the source such that an aspect of the aberrated image varies when the distance between the reference plane of the object and the reference plane the optical system changes; sensing the aberrated image with an optical sensor; and determining the distance from the reference plane of the optical measurement instrument to the reference plane of the object under test based on an aspect of an aberrated image sensed by the optical sensor (e.g., based on a shape, aspect ratio, or intensity distribution of the aberrated image, or some portion thereof). In some embodiments, the aspect of the aberrated image varies between when the distance is greater than a nominal distance $D_{NOM}$, and when the distance is less than $D_{NOM}$, the variation being different in a first direction than in a second direction perpendicular to the first direction. In some embodiments, the source is dimensioned to form or approximate a point source. In other embodiments, the method includes illuminating the test object with a light pattern comprising two or more sources.

In another aspect of the invention, a system is provided for measuring a distance from a reference plane of an optical measurement instrument to a reference plane of an optical device under test. The system comprises: an illumination system adapted to illuminate the object under test; an optical system adapted to receive light from the object under test and to produce an aberrated image; an optical sensor adapted to receive and sense the aberrated image; and a processor adapted to determine the distance from the reference plane of the optical measurement instrument to the reference plane of the optical device based on an aspect of the aberrated image sensed by the optical sensor (e.g., based on a shape, aspect ratio, or intensity distribution of the aberrated image, or some portion thereof). In some embodiments, the aberrated image is formed such that an aspect of the aberrated image varies between when the distance is greater than a nominal distance $D_{NOM}$, and when the distance is less than $D_{NOM}$, the variation being different in a first direction than in a second direction perpendicular to the first direction. In some embodiments, the illumination system comprises source that is dimensioned to form or approximate a point source. In other embodiments, the illumination system comprises a light pattern having two or more sources.

In yet another aspect of the invention, a system is provided for measuring a distance from a reference plane of an optical measurement instrument to a reference plane of an object under test. The system comprises: an illumination system for providing a pattern of light to the object under test; an optical system which forms an astigmatic image of the pattern of light; an optical sensor adapted to receive the astigmatic image; and a processor adapted to determine the distance from the reference plane of the optical measurement instrument to the reference plane of the optical device based on an aspect of the astigmatic image sensed by the optical sensor (e.g., based on a shape, aspect ratio, or intensity distribution of the aberrated image, or some portion thereof).

DETAILED DESCRIPTION

Disclosed below are systems and methods that utilize an aberration introduced by an optical system to determine the Z-Distance of an optical measurement system to an object under test, such as an eye or other optical system or component.

Figure 1:
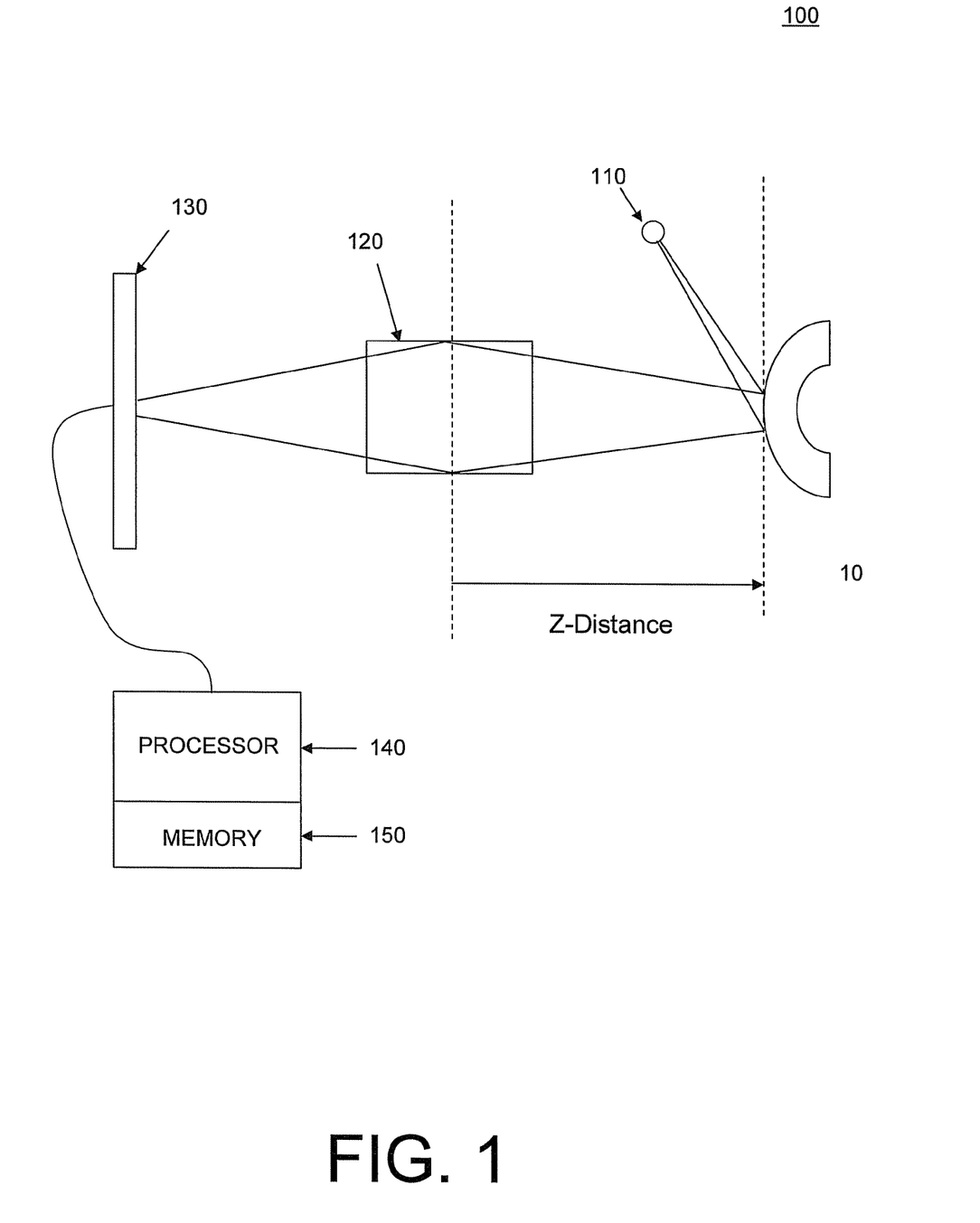
FIG. 1 illustrates a system for measuring the distance from a reference plane of an optical measurement instrument to a reference plane of an object under test.

FIG. 1 illustrates a system 100 for measuring the distance from a reference plane 105 for an optical measurement instrument to a reference plane 15 of an object under test 10.

System 100 includes an illumination system 110, an optical system 120, an optical sensor 130, a processor 140, and memory 150.

System 100 may be integrated with an optical measurement instrument, or may be configured as a standalone system that can be employed at the start of an optical measurement to determine the distance from the reference plane 105 for the optical measurement instrument to a reference plane 15 of object under test 10 (hereinafter referred to as "the Z-Distance") to maintain the accuracy of measurements made by the optical measurement instrument. The reference plane 105 for the optical measurement instrument can be chosen as any plane that is convenient for measurement purposes. In one embodiment the reference plane 105 may pass through optical system 120.

Illumination system 110 illuminates object under test 10 with a predetermined pattern comprising one or more sources of light. An exemplary embodiment of illumination system 110 will be described in greater detail below with respect to FIGS. 3 and 4.

Optical system 120 introduces an aberration into a received light pattern such that at least one aspect of the light pattern and/or the one or more sources of light varies asymmetrically, for example, varies asymmetrically about a nominal Z-Distance ("$D_{NOM}$") in orthogonal first and second directions. That is, as the light pattern, and individual sources therein, passes through optical system 120, at least one aspect of the light pattern and/or sources change differently in the X-direction ("into the page" in FIG. 1) than it does in the Y-direction as the Z-Distance changes, for example, from being less than some nominal distance $D_{NOM}$ to being greater than $D_{NOM}$.

In operation, illumination system 110 illuminates object under test 10 with light having a predetermined pattern. At least a portion of the pattern of light that illuminates object under test 10 is scattered or reflected or both toward optical system 120. Optical system 120 produces an aberrated image of the predetermined pattern or portion or light source thereof, as described above.

Optical sensor 130 receives the aberrated image produced by optical system 120 and outputs detected image data. Optical sensor 130 may comprise a photoreceptive sensor, such as a charge-coupled device (CCD) or a complementary metal oxide semiconductor (CMOS) detector.

Processor 140 receives the detected image data and uses the detected image data to determine the Z-Distance. In particular, processor 140 determines the Z-Distance based on an aspect of an aberrated image of the light pattern and/or the individual sources contained therein. In one embodiment, a characteristic of the sensed light is compared to reference data stored in memory 150. In that case, an object having a known radius of curvature may be used to generate at least one set of reference data as a function of the distance between reference plane 105 and the object having the known radius of curvature. For ease of comparison, the reference data may be fitted to a reference curve using a polynomial function or other convenient function.

Figure 2A:
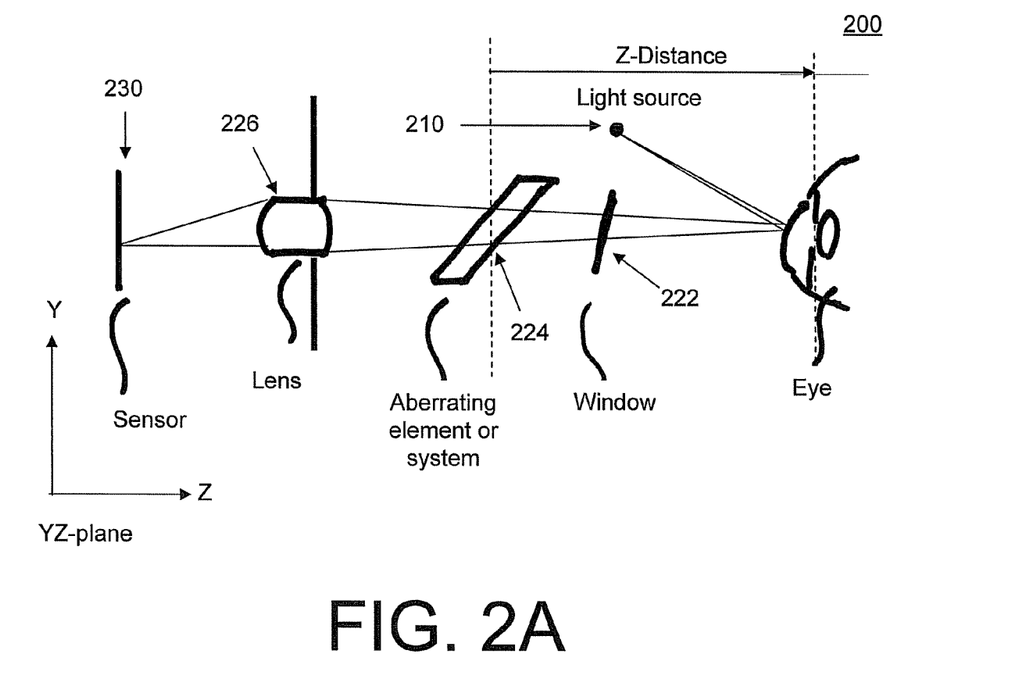
FIGS. 2A-B illustrate one embodiment of the system of FIG. 1.
Figure 2B:
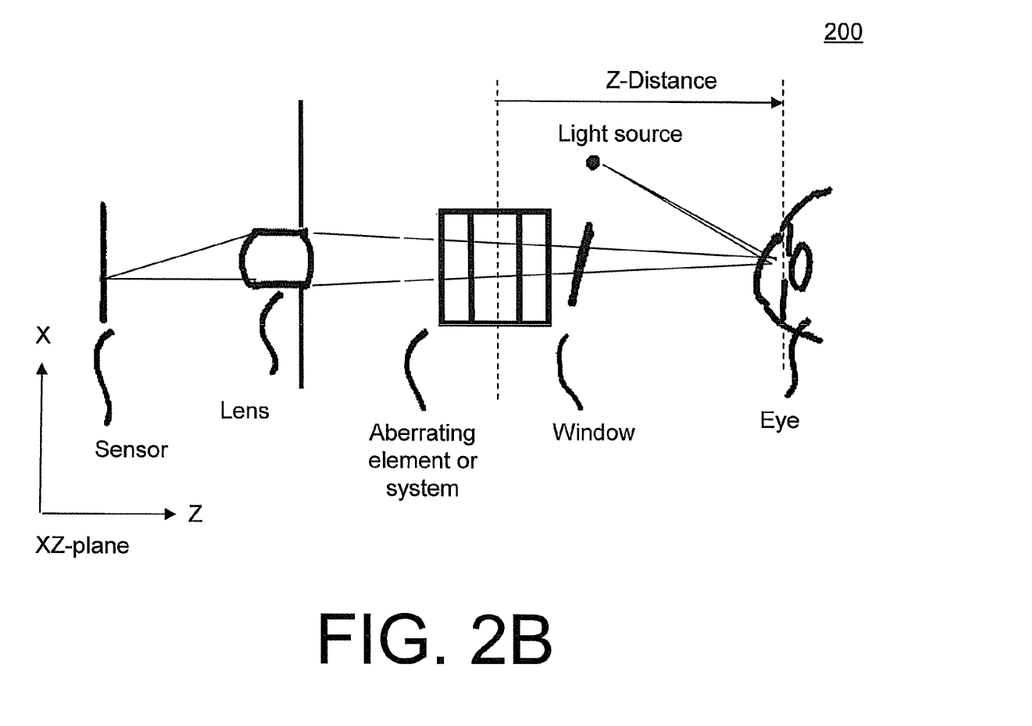

FIGS. 2A-B illustrate one embodiment 200 of the system of FIG. 1. FIG. 2A is a view of system 200 in a first plane labeled the YZ-plane. FIG. 2B is a view of system 200 in a second plane, labeled the XZ-plane, that is perpendicular to the first plane.

System 200 includes an illumination system 210, an optional window 222, an optical element 224, a lens 226, an optical sensor 230, and a processor (not shown in FIGS. 2A-B) and memory (also not shown in FIGS. 2A-B). In the illustrated embodiment, the optical element 224 comprises a plate beam splitter that is tilted relative to a system optical axis. As perhaps best seen in FIG. 2A, plate beamsplitter 224 is tilted in the Z-direction. In general, the optical element 224 may be replace by, or used to approximate, any combination of optics of an optical system, for example, a combination of optics forming at least part of a wavefront measurement system and/or a topographic measurement system.

As in the case of system 100, system 200 may be integrated with an optical measurement instrument, or may be configured as a standalone system that can be employed at the start of a measurement to determine the Z-Distance to maintain the accuracy of measurements made by the optical measurement instrument.

Illumination system 210 illuminates object under test 10 with a predetermined pattern. An exemplary embodiment of illumination system 110 and 210 will be described in greater detail below with respect to FIGS. 3 and 4.

The combination of plate beamsplitter 224 and lens 226 produce an aberrated image of the light pattern and/or the individual sources contained therein. In particular, as the light pattern passes through the combination of plate beamsplitter 224 and lens 226, the "length" or size of the light pattern changes differently in the X-direction than it does in the Y-direction as the Z-Distance changes from being less than some nominal distance $D_{NOM}$ to being greater than $D_{NOM}$. This is due to the astigmatism introduced by the system. Astigmatism, as is well known to one skilled in the art, is a difference in effective lens power along different meridians. Thus the lens 226 and beamsplitter combination 224 effectively has different focal lengths in the YZ plane than for the XZ plane. The aberration introduced into an image of the light pattern may be as simple as a single spot of light, a plurality of spots of light, or an extended source. The light pattern may also comprised of a collection of smaller light patterns. The analysis for calculating distance may be applied to the entire pattern, or to the individual constituents or sources making up the light pattern.

The astigmatic element creates an image of the source 210 onto the sensor 230 which has finite size corresponding to the rays that are in proper focus. For the example shown in FIGS. 2A&B, the lens 226 and beamsplitter 224 combination effectively has a slightly smaller focal length in the YZ plane than in the XY plane. Thus the image of the source 210 in the XZ plane will achieve a focus when the test object 210 is slightly closer to the instrument (Z-distance is shorter than Dnom). Conversely, in the YZ plane, the image of the source 210 will achieve optimal focus when the object is slightly further from the instrument (Z-distance is longer than Dnom).

The net result is that the shape of the image changes as the object is moved closer and further from the instrument. That is, when the object is closer than the nominal distance, then the aberrated image is smaller in the x-direction and larger in the y-direction. When the object is slightly further, then the image is slightly larger in the x-direction and slightly smaller in the Y-direction.

At the nominal distance (Dnom) the image is arranged so that the image appears approximately symmetrical in x- and y. This is called the circle of least confusion, and is well known to those skilled in the art. The actual z-distance from some physical instrument component may in general be different from this reference plane, however, it is straightforward to add the appropriate offset to the measurement distance if needed as this would be just a constant offset.

Optical sensor 230 receives and senses the light from lens 226 and outputs detected image data. Optical sensor 230 may comprise a photoreceptive sensor, such as a charge-coupled device (CCD) or a complementary metal oxide semiconductor (CMOS) detector.

A processor receives the detected image data and uses the detected image data to determine the Z-Distance. In particular, processor 140 determines the Z-Distance based on the astigmatism of the light sensed by optical sensor 230.

To better illustrate the operation of system 200, a concrete example will now be described with a particular light pattern in a case where the object under test is a human eye.

Figure 3:
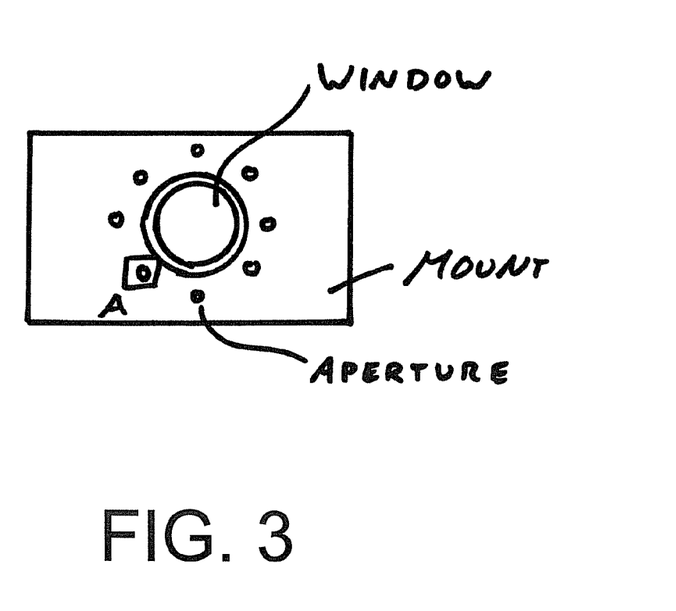
FIG. 3 illustrates an illumination source that may be employed in the systems of FIGS. 1 and 2A-B.
Figure 4:
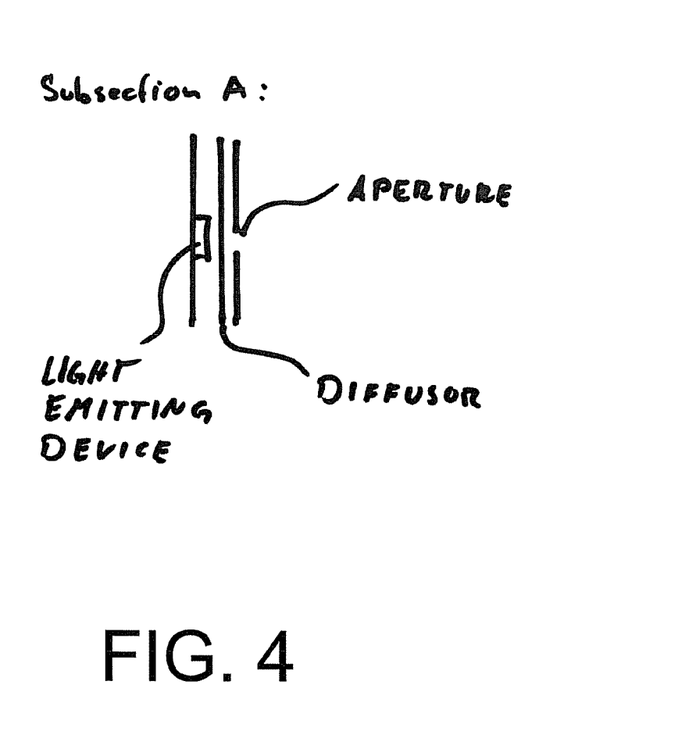
FIG. 4 is a cross-section of the illumination source of FIG. 3.

FIG. 3 illustrates an illumination system 300 that may be employed in the illumination systems 110, 210 of FIGS. 1 and 2A-B. FIG. 4 is a cross-section of the illumination source of FIG. 3. In one embodiment, illumination system 300 may comprise an infrared or low power visible emitter, a diffuser to provide a predetermined intensity distribution, and an aperture forming source 301 of defined dimensions. The source 301 may be dimensioned to form or approximate a point source. Alternatively, one or more source 301 may be dimensioned to form an extended source, for example, to provide additional information, of the test object and/or an optical system. In some embodiments, the source 301 is much smaller than a reference distance, for example, the z-distance in FIGS. 1, 2A, 2B or a distance to a first lens or optical element in an optical system. Infrared illumination has the benefit of being invisible to the human eye and therefore does not generally contribute to a decrease of pupil size in a non dilated state. This may be important if the optical measurement instrument is a wavefront aberrometer, because in such a system the human pupil of the eye is the limiting aperture in the imaging process. Thus the functions of the z-distance measurement would not interfere with other functions of the device. Illumination system 300 may comprise only one spot 301, or a ring of several spots 301, for example, to obtain an average value, which decreases ambiguities due to varying ambient light conditions or manufacturing tolerances of the light emitting device. In FIGS. 3-4 a pattern of spots is shown to provide for averaging, while covering a symmetric area around the optical axis of the optical measurement instrument and maintaining an equal distance of each spot to the axis.

The spot-source 301 shown in FIG. 4 can be provided for each of the apertures in the mount shown in FIG. 3.

For example, if the object under test is a human eye is positioned in a near range around the nominal working distance of an optical measuring instrument, each spot is first reflected by the cornea, which in a simple approximation acts as a spherical mirror, to form a virtual image behind the mirror. This image, created by reflected irradiation off the anterior surface of the cornea is also known as the first Purkinje Image (PKI), which for the vast majority of human eyes lies very near the iris plane. Hence a focused PKI brings the optical measuring instrument into the working distance if the goal is to image to a plane conjugate to the iris or exit pupil of the eye, as in a wavefront aberrometer system. If this is not the case, as in a corneal topographer or Keratometer, the offset to that plane can be applied using statistical values which are widely available in published literature.

The virtual image or PKI then acts as a source itself and is imaged onto optical sensor 130 or 230. In doing so, it passes through an aberrating optical system, such as optical system 120 or the system comprising the combination of plate beamsplitter 234 and lens 236, and optionally window 222.

Figure 5A:
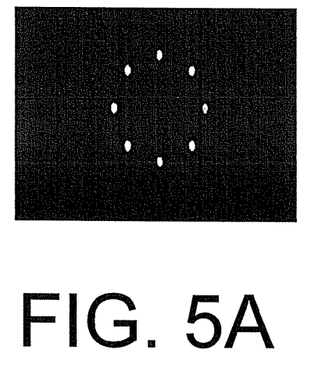
FIGS. 5A-C illustrate possible image patterns in the arrangement of FIGS. 2A-B for various Z-Distances.
Figure 5B:
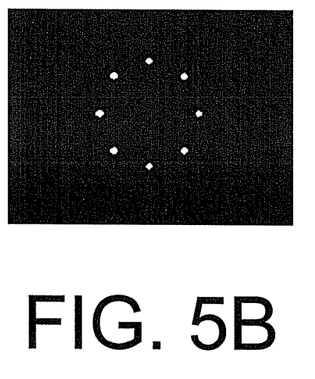
Figure 5C:
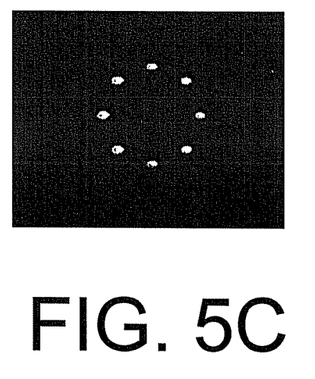

FIGS. 5A-C illustrate possible image patterns generated by the arrangement of FIG. 1 or 2A-B for various Z-Distances. Depending on the position of the eye relative to the focal plane or nominal Z-Distance, different patterns of individual spot images are possible on optical sensor 130/230. FIG. 5A shows an example where the Z-Distance is less than a nominal distance, $D_{NOM}$. FIG. 5C shows an example where the Z-Distance is greater than the nominal distance, $D_{NOM}$. FIG. 58 shows an example where the Z-Distance is about equal to the nominal distance, $D_{NOM}$.

Still referring to FIGS. 5A-C, in certain embodiments, an aspect of one or more spots in a image are measured and analyzed to determine a distance of an object from an optical system. For examples, certain spots may be selected based on the value of a figure of merit related to the quality of the spot images. In some embodiments, data for two or more spots are combined to provide a better measurement of the distance between the object and the optical system. In yet other embodiments, one or more aspects of an overall image pattern formed by two or more imaged spots from an illuminating source pattern are measured. The measurement data may be used in combination with data for individually imaged spots, for example, to enhance the distance measurement and/or to obtain other information about the system or test object, such as the shape of the test object or an aberration of the test object.

Figure 6:
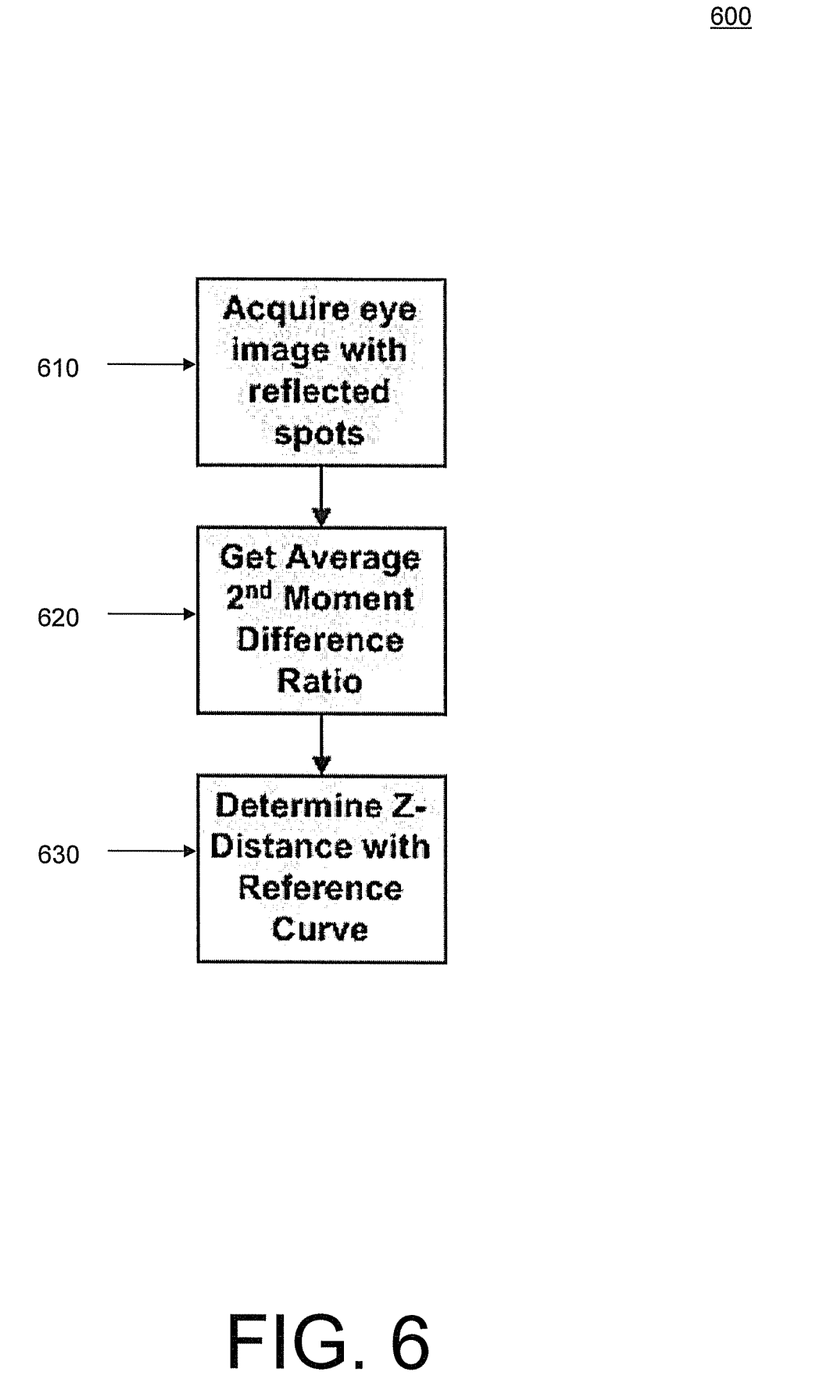
FIG. 6 illustrates one embodiment of a method of determining Z-Distance using the arrangement in FIGS. 2A-B.

FIG. 6 illustrates one embodiment of a method of determining the Z-Distance using the arrangement in FIGS. 2A-B. In a step 610, image data is collected by optical sensor 230. In a step 620, a characteristic is determined for the senses image. In particular, an average $2^{nd}$ moment difference ratio may be calculated for the sensed image, as explained in greater detail below. Finally, in a step 630, the $2^{nd}$ moment difference ratio and/or other information is compared to reference data, for example by mapping $2^{nd}$ moment difference ratio to Z-Distance, as explained in further detail below.

Figure 7:
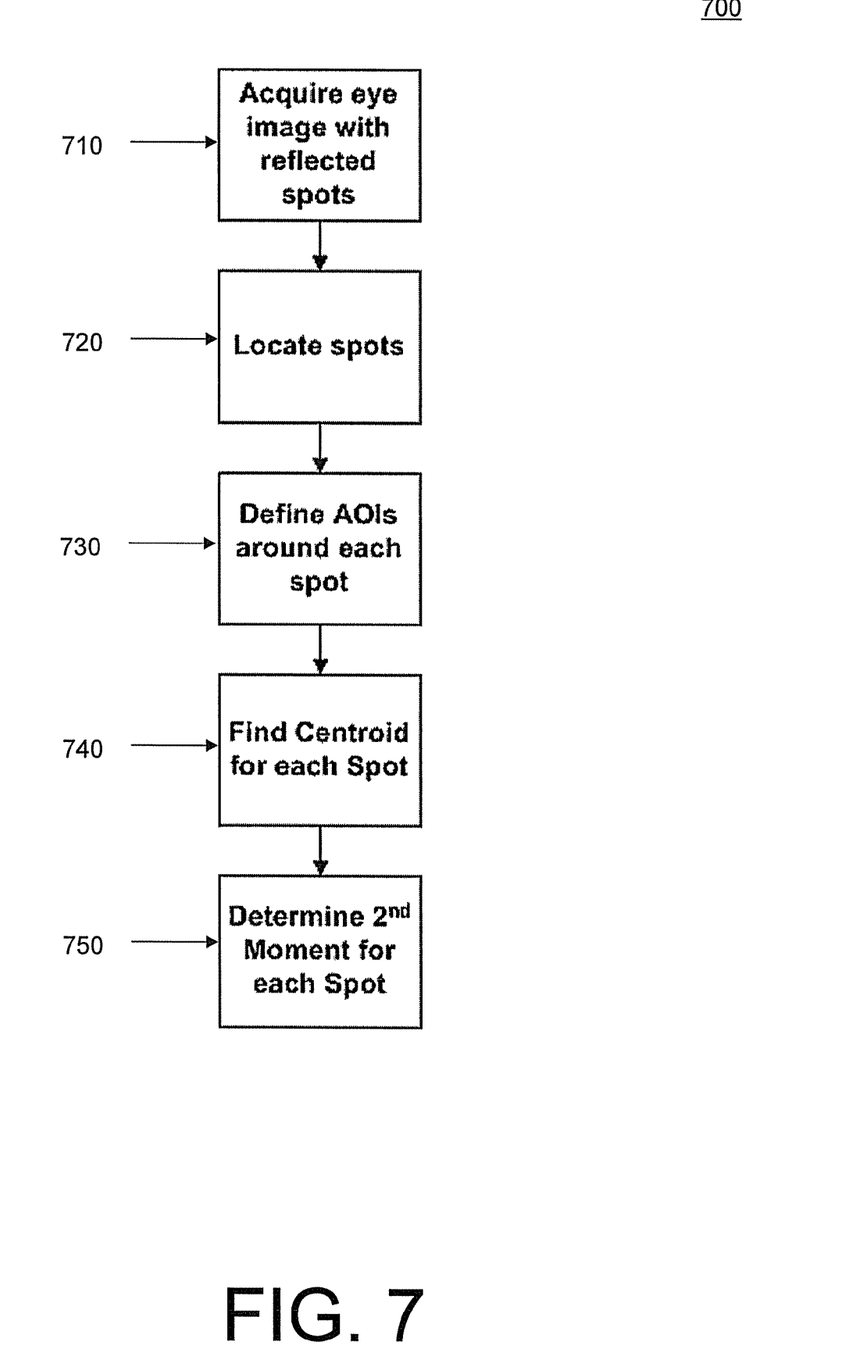
FIG. 7 illustrates one embodiment of a method of determining second moments for each spot of an image sensed by an optical sensor.

FIG. 7 illustrates one embodiment of a method of determining second moments for each spot of an image sensed by optical sensor 230 in FIGS. 2A-B. In a step 710, image data is collected by optical sensor 230. In a step 720, spots are located using the image data. In a step 730, areas of interest (AOIs) are defined around each spot. In a step 740, the centroid is found for each spot. Finally, in a step 750, the second moment is calculated for each spot.

Computational analysis of the image data from optical sensor 230, which can comprise a pattern recognition algorithm or edge detection algorithm, can be employed to locate each spot and allow for setting of areas of interest and the computation of centroids.

One method of computing centroids $(x_0, y_0)$ in X and Y directions is given in equations (1a-1b):

$$x_0 = \frac{\sum I \times x}{\sum I} \qquad (1a)$$

$$y_0 = \frac{\sum I \times y}{\sum I}, \quad (1b)$$

where I may be the actual pixel values or be constructed by thresholding or otherwise processing these values.

With this data, the spot size in X and Y direction scan be computed. One convenient mathematical method for calculating the spot size is to use the $2^{nd}$ moment calculation method. The second moments may be defined as in equations (2a-2b):

$$2M_X = \frac{\sum I \times (x - x_0)^2}{\sum I} \quad (2a)$$

$$2M_Y = \frac{\sum I \times (y - y_0)^2}{\sum I} \quad (2b)$$

To calculate a relative difference ratio of $2^{nd}$ moment data in the X and Y directions, we divide the difference through the sum as shown in equation (3):

$$DR = \frac{2M_x - 2M_y}{2M_x + 2M_y} \quad (3)$$

To compensate for uneven illumination, whether caused by variances in the light emitting devices or ambient light conditions or obstacles in the optical path (e.g. dust), in one embodiment, the average second moment difference ratio DR is calculated for a plurality of light spots by, for example, using a ring of light spots as illustrated above in FIG. 3.

In practice, in one embodiment a user positions the system 200 into a range around a nominal working distance, where the imaged spots are defocused, for example, to a degree where they can be reliably located by pattern recognition or edge detection algorithms. For this purpose this is implemented in a "live" mode, where the user of the instrument can adjust the distance while inspecting the in-range or out-of-range condition on a display.

After positioning and acquisition of the image, the spots are located and the 2nd Moments for each spot, or selected spots, are calculated using Equations 2a-2b above, for example by a processor connected to an output of optical sensor 230 such as the processor 140 of FIG. 1. The second moment difference ratio is calculated as in Equation 3. The second moment difference ratio depends uniquely upon the Z-Distance, and so the Z-Distance can be determined with fit polynomial coefficients describing a reference curve, as explained below.

Figure 8:
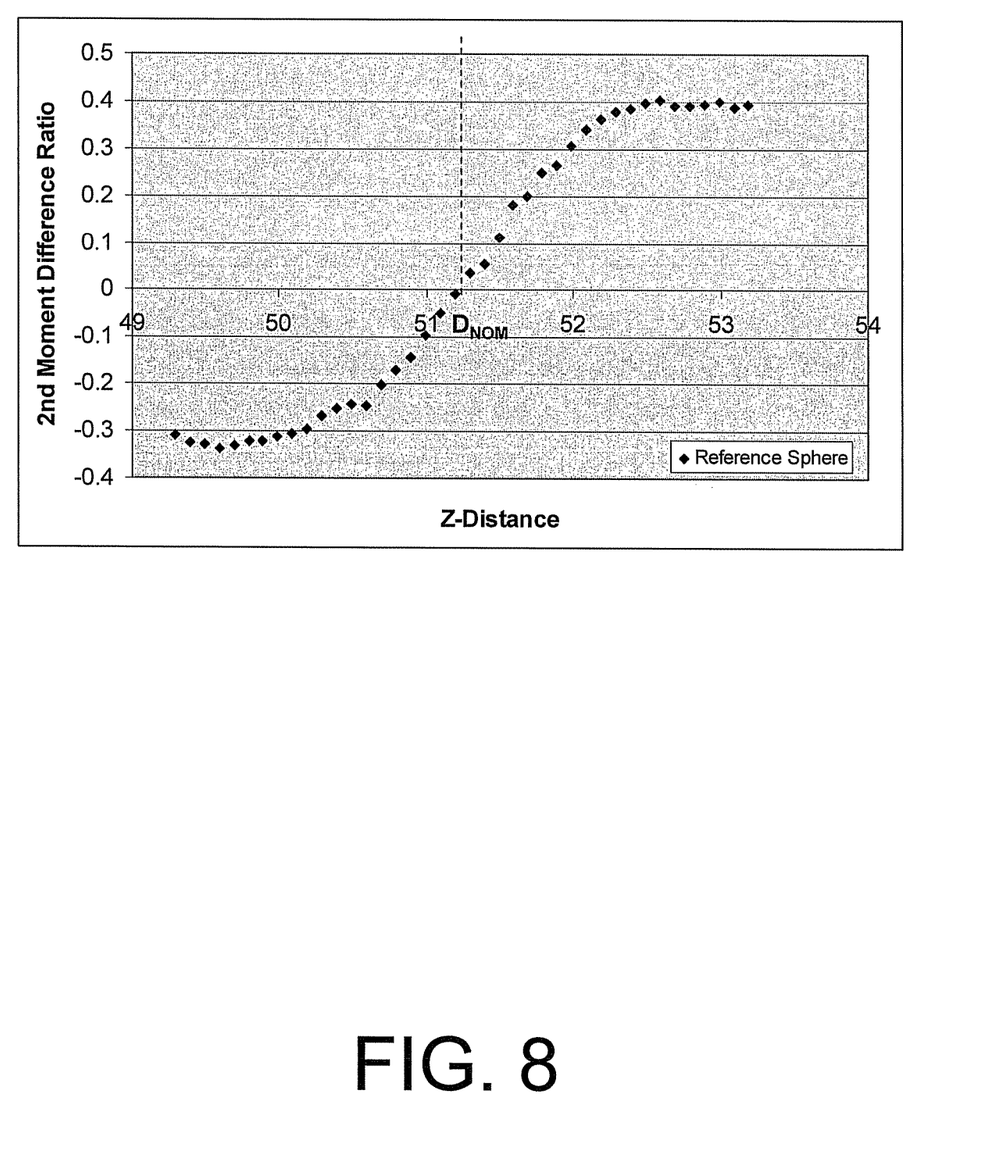
FIG. 8 is a graph showing one embodiment of a reference curve exhibiting a relationship between second moment difference ratio and Z-Distance in the system of FIGS. 2A-B.

FIG. 8 is a graph showing one embodiment of a reference curve obtained from measured reference data exhibiting a relationship between second moment ratio and Z-distance in the system of FIGS. 2A-B.

This graph can be experimentally obtained for one or more objects under test with a known radius of curvature. These can be a set of calibrated metal ball bearings obtained from a ball bearing gauge set. The range of radii of curvature can include the statistical range of radii of curvature of human corneas. The 2nd moment difference ratio data versus Z-Distance is calculated for one or more known spheres and stored in memory (e.g., memory 150) as reference data. The references data can be used to generate one or more analytical curves, for example with an n order polynomial fit, as illustrated in Equation (4).

$$DR = c_0 + c_1 z + c_2 z^2 + \ldots + c_n z^n \quad (4)$$

The fit polynomial coefficients $c_1$ through $c_n$ can stored in a memory (e.g., memory 150) for the computation of the Z-Distance of an image from an unknown surface. These curves are hereinafter called "Reference Curves."

In certain embodiments, derived data such as that provided by Equation (3) or illustrated in FIG. 8 is used to determine when an object is within a predetermined range. For example, using the curve illustrated in FIG. 8, if the calculated $2^{nd}$ moment difference ratio for a given measurement falls within a range of −0.2 to +0.3, than an "in range" signal may be generated to inform a user that an object or subject is located at a suitable distance for making a diagnostic measurement of the object or subject (e.g., for making a wavefront or topographic measurement). If the calculated $2^{nd}$ moment difference ratio for a given measurement is less than −0.2, then a "too close" signal may be generated to inform a user that an object or subject is located too close to make a diagnostic measurement of the object or subject. Conversely, if the calculated $2^{nd}$ moment difference ratio for a given measurement is greater than +0.3, then a "too far" may be generated to inform a user that an object or subject is located too far away to make a diagnostic measurement of the object or subject.

In other embodiments, data such as that provided by Equation (3) or illustrated in FIG. 8 is used to make a more accurate measurement than that provided in the previous paragraph. For example, an exact value of a calculated $2^{nd}$ moment difference ratio may be used to determine a distance of an object from an optical system. In some embodiments, such information may be used alone or in combination with other data (e.g., an overall shape or other aspect of the spot illustrated in FIG. 5) to refine or enhance the distance measurement, for example, by determining or estimating a shape or aberration of the test object. In this manner, one or more new equations, equation parameters, or and/or corrected reference curves similar to that shown in FIG. 8 may be calculated so as to allow a refined or more accurate distance measurement to be made.

Figure 9:
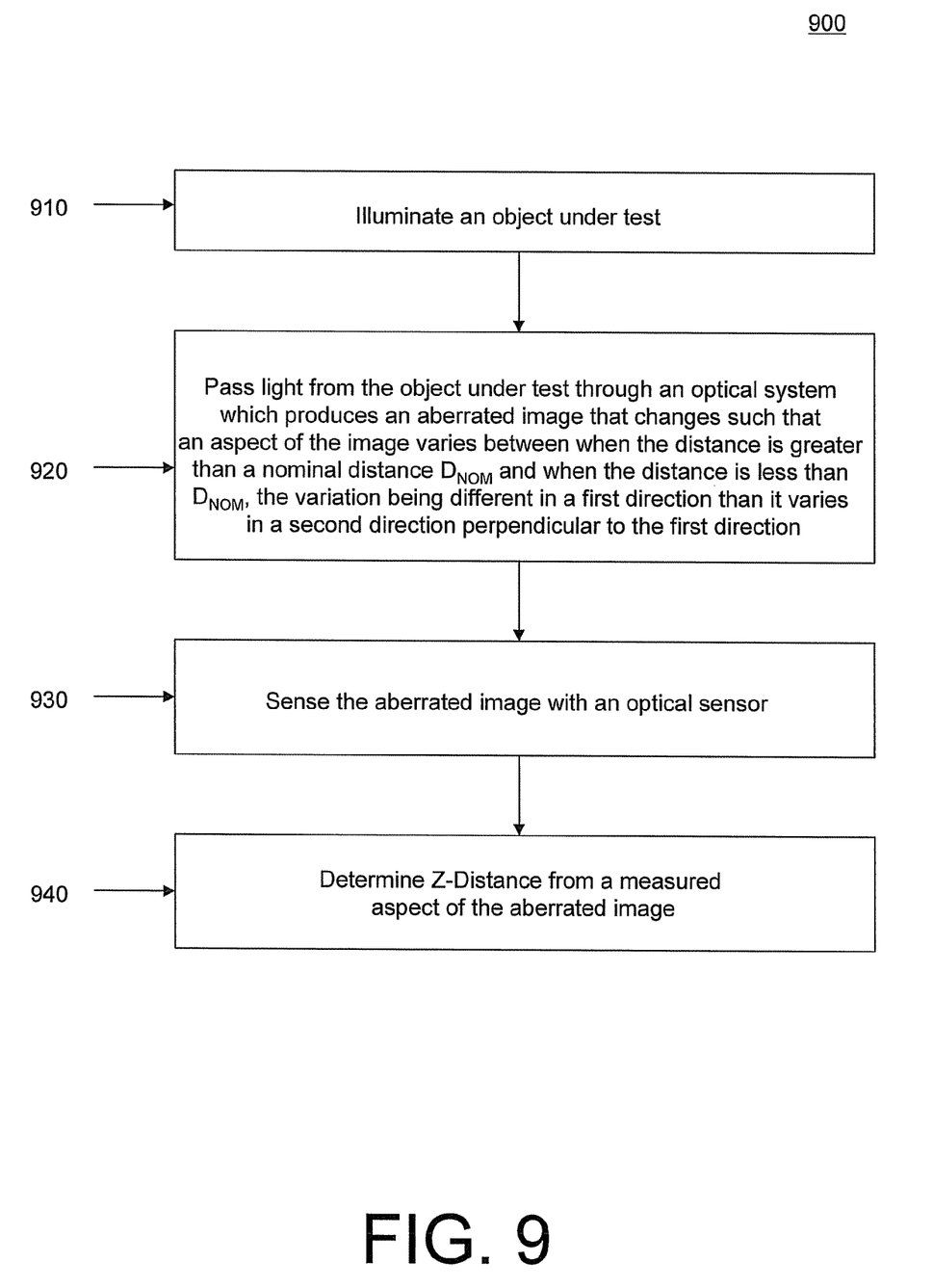
FIG. 9 illustrates another embodiment of a method of determining Z-Distance using the arrangement in FIG. 1.

FIG. 9 illustrates another embodiment of a method of determining Z-Distance using the arrangement in FIG. 1.

In a step 910, an object under test is illuminated.

In a step 920, light from the object under test is passed through an optical system which produces an aberrated image that changes such that an aspect of the image varies between when the distance is greater than a nominal distance $D_{NOM}$ and when the distance is less than $D_{NOM}$, the variation being different in a first direction than in a second direction perpendicular to the first direction.

In a step 930, the aberrated image is sensed with an optical sensor.

In a step 940, the distance from the reference plane of the optical measurement instrument to the reference plane of the object under test is determined based on a measured aspect of the aberrated image sensed by the optical sensor.

Figure 10:
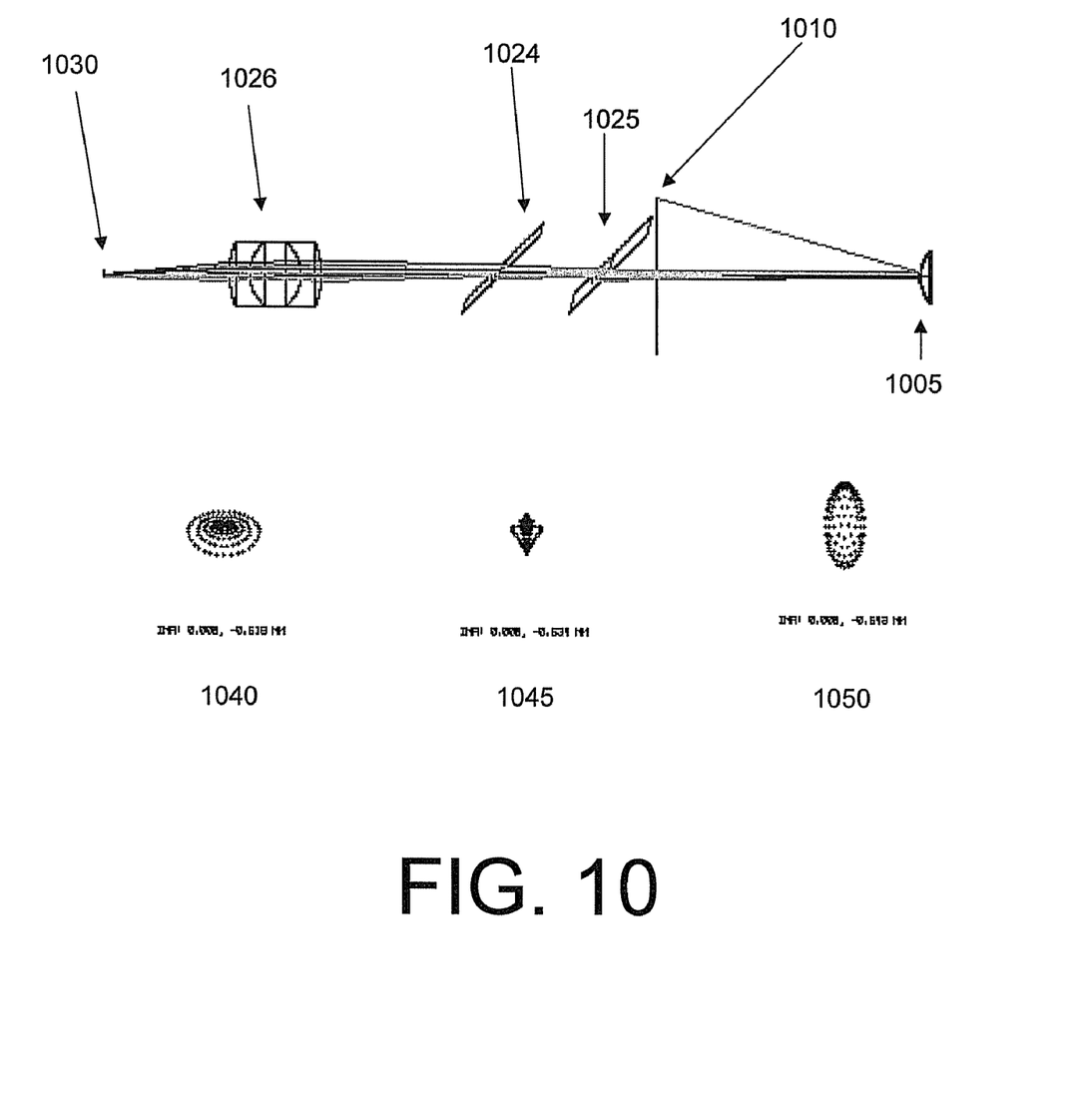
FIG. 10 illustrates an optical ray trace

FIG. 10 depicts an optical ray trace diagram of an embodiment of the present invention. In this embodiment, there are two beamsplitters 1024 and 1025 to provide a predetermined amount of astigmatism. The lens 1026 and beamsplitters 1024 and 1025 are shown widely separated. The position of the beamsplitters 1024 and 1025 relative to the lens 1026 or object under test 1005 is relatively unimportant. As illustrated in FIG. 10, the source 1010 in this case is located near the first beamsplitter 1025 as a matter of convenience, but is not constrained to this location. The spot diagrams 1040, 1045, 1050 illustrate the change is shape at the sensor 1030 a test object 1005 is moved relative to the beamsplitter 1025. In some embodiments, a reference distance is set to correspond to the distance between the test object 1005 and the beamsplitter 1025 that produces the smallest focus (e.g., illustrated by the spot diagram 1045).

In the several of the embodiments described above astigmatism was used as the exemplary aberration. However, there are many possible aberrations that may be introduced by, for example, the systems in FIG. 1, 2A, 2B, or 10, and/or added to the imaging path of these systems that could accomplish the desired objective. Generally, an added aberration or combination of aberrations create images that are different in appearance or in a particular aspect as the instrument is moved closer vs. further from the object under test. Defocus, for example, would not generally provide the needed information, since it adds an aberration to the images that is symmetrically disposed about the desired plane, thus making it more difficult for an algorithm to correctly indicate which direction the instrument should be adjusted to obtain a desired position. However, a spherical aberration could be substituted or added to obtain the desired result. In the case of spherical aberrations the appearance of the spot images would change asymmetrically as the instrument is moved relative to the object under test in one direction or another relative to a reference distance. For spherical aberration the images generally appear as rings when (for example) the instrument is too close and as bright spots with halos when (for example) the instrument is too far. Other potential aberrations include but are not limited to coma, trefoil, or any other aberration that changes the image asymmetrically.

Embodiments of the system and method described above can be employed with a variety of optical measurement instruments such as eye examination instruments, including ophthalmic diagnostic and/or therapeutic instruments. Examples of such eye examination instruments include wavefront aberrometers, autorefractors, corneal topographers and other instruments which require the knowledge of precise distance of the measurement device to a reference plane of the optical system under test, to perform measurements such as wavefront measurement of the human eye, topography of a human cornea or optical coherence tomography of the human cornea, vitreous humor and tens. The object under test can be, but is not limited to, a human eye, a contact lens, an intraocular lens (IOL), or another object in a wet (hydrated and/or containing liquid film on its surface) or dry state. With the true distance to the object under test, or the difference between the true distance and a nominal distance, being known, then measurement results can be recomputed or corrected to achieve the highest possible measurement accuracy.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

We claim:

1. A method of measuring a distance from a reference plane of an optical measurement instrument to a reference plane of an object under test, comprising:

illuminating the object under test with a source;

passing light from the object under test through an optical system having at least one optical aberration;

producing an aberrated image of at least a portion of the source from the light passed through the optical system from the object under test;

sensing the aberrated image with an optical sensor; and determining the distance from the reference plane of the optical measurement instrument to the reference plane of the object under test based on an aspect of the aberrated image sensed by the optical sensor.

2. The method of claim 1, wherein illuminating the object under test comprises directing a symmetrical pattern of light spots onto the object under test.

3. The method of claim 1, wherein the object under test is a human eye, and wherein the method further comprises measuring an optical property of the human eye based on the distance from the reference plane of the optical measurement instrument to a reference plane of the human eye.

4. The method of claim 1, wherein the object under test is one of an intraocular lens and a contact lens.

5. The method of claim 1 wherein the optical instrument is an ophthalmic or optometric diagnostic instrument, and wherein the method further comprises measuring the distance from the reference plane of the optical measurement instrument to a reference plane of the human eye with the diagnostic instrument.

6. The method of claim 1, wherein the optical system includes an astigmatic element which applies astigmatism to the light from the object under test.

7. The method of claim 1, wherein passing the light from the object under test through the optical system comprises:

passing the light through a plate beamsplitter tilted in a third direction perpendicular to the first and second directions; and passing light from the plate beamsplitter through a lens.

8. The method of claim 1, further comprising using an object having a known radius of curvature to generate at least one set of reference data as a function of distance between the reference plane of the optical measurement instrument and the object having the known radius of curvature, wherein determining the distance from the reference plane of the optical measurement instrument to the reference plane of the optical device under test comprises comparing a characteristic of the aberrated image sensed by the optical sensor to the reference data.

9. The method of claim 1, further comprising adjusting the relative position of the object under test to the instrument until a desired value is obtained.

10. The method of claim 1, wherein the aspect of the aberrated image varies between when the distance is greater than a nominal distance $D_{NOM}$, and when the distance is less than $D_{NOM}$, the variation being different in a first direction than in a second direction perpendicular to the first direction.

11. A system for measuring a distance from a reference plane of an optical measurement instrument to a reference plane of an object under test, comprising:

an illumination system configured to illuminate the object under test;

an optical system configured to receive light from the object under test and to produce an aberrated image from the light received from the object under test;

an optical sensor configured to receive and sense the aberrated image; and a processor coupled to the optical sensor and configured to determine the distance from the reference plane of the optical measurement instrument to the reference plane of the object based on an aspect of the aberrated image sensed by the optical sensor.

12. The system of claim 11, wherein the illumination system comprises a symmetrical pattern of light sources.

13. The system of claim 11, wherein the object under test is a human eye.

14. The system of claim 11, wherein the object under test is one of an intraocular lens and a contact lens.

15. The system of claim 11, wherein the optical instrument is an ophthalmic or optometric diagnostic instrument.

16. The system of claim 11, wherein the optical system includes an astigmatic element which applies astigmatism to the light from the object under test.

17. The system of claim 11, wherein the optical system comprises:
    a plate beamsplitter tilted in a third direction perpendicular to the first and second directions; and
    a lens arranged to receive light from the plate beamsplitter.

18. The system of claim 11, further comprising a memory coupled to the processor for storing reference data for a plurality of distances between the reference plane of the optical measurement instrument and an object having the known radius of curvature.

19. The system of claim 11, wherein the aspect of the aberrated image is an aspect ratio of the aberrated image or a $2^{nd}$ moment difference ratio.

20. A system for measuring a distance from a reference plane of an optical measurement instrument to a reference plane of an object under test, comprising:
    an illumination system for providing a pattern of light to the object under test;
    an optical system which produces an astigmatic image of the pattern of light;
    an optical sensor adapted to receive and sense the astigmatic image of the pattern of light; and
    a processor coupled to the optical sensor and adapted to determine the distance from the reference plane of the optical measurement instrument to the reference plane of the object based on an aspect of the astigmatic image sensed by the optical sensor.

21. The system of claim 20, wherein the processor is configured to calculate a $2^{nd}$ moment difference ratio of the astigmatic image of the pattern of light, DR, where $$DR = \frac{2M_x - 2M_y}{2M_x + 2M_y},$$

where $2M_X$ is the second moment of the astigmatic image in a first direction, and $2M_Y$ is the second moment of the astigmatic image in a second direction perpendicular to the first direction.

22. The system of claim 20, wherein the optical system comprises:
    a plate beamsplitter tilted in a third direction perpendicular to the first and second directions; and
    a lens arranged to receive light from the plate beamsplitter.

23. The system of claim 20, wherein the illumination system comprises a plurality of light sources arranged in a ring.

* * * * *